ately retained by the products through the selective high efficiency conversion of coal to a low ratio syngas utilizing a portion of the Fischer-Tropsch generated heat recovered as steam, conversion of the low ratio syngas with a water gas shift F-T catalyst to a product comprising $C_1$ to $C_{50}$ hydrocarbons and oxygenates, converting the F-T product to premium gas and increased liquid fuels comprising gasoline and distillate with a special zeolite catalyst and recovering the SNG and LPG products of the selective steps to provide an improved product slate. A portion of the produced fuel gas is used in lieu of coal to provide some of the heat energy requirements of the combination process.

United States Patent [19]
Haag et al.

[11] 4,252,736
[45] Feb. 24, 1981

[54] CONVERSION OF SYNTHESIS GAS TO HYDROCARBON MIXTURES UTILIZING DUAL REACTORS

[75] Inventors: Werner O. Haag, Lawrenceville; Tracy J. Huang, Trenton; James W. Kuo, Cherry Hill, all of N.J.; Reuel Shinnar, Great Neck, N.Y.

[73] Assignee: Mobil Oil Corporation, Fairfax, Va.

[21] Appl. No.: 44,873

[22] Filed: Jun. 1, 1979

[51] Int. Cl.³ .............................................. C07C 1/04
[52] U.S. Cl. .................................. 260/450; 260/449 R; 260/449 L; 260/449.1 R; 208/950; 585/310; 585/469; 585/407; 585/603; 585/638; 585/733
[58] Field of Search ........ 260/449 R, 449 L, 449.6 R, 260/450; 208/950; 585/310, 469, 603, 407, 638, 733

[56] References Cited

U.S. PATENT DOCUMENTS

| | | | |
|---|---|---|---|
| 2,361,997 | 11/1944 | Dreyfus | 260/449 L |
| 2,438,029 | 3/1948 | Atwell | 260/449 R |
| 2,440,109 | 4/1948 | Moore | 260/449 R |
| 2,680,126 | 6/1954 | Atwell | 260/449 L |
| 2,798,888 | 4/1957 | Tenney et al. | 260/449 L |
| 4,041,097 | 8/1977 | Ireland et al. | 260/449 R |
| 4,046,829 | 9/1977 | Ireland et al. | 260/449 R |

OTHER PUBLICATIONS

Hoogendoorn, Clean Fuels from Coal, Symposium II, presented Jun. 23-27, 1975, Sponsor by Institute of Gas Technology, pp. 343-358.
Kolbel, Chemie Ing. Techn., 28, No. 6, 1956, pp. 381-440.

*Primary Examiner*—Howard T. Mars
*Attorney, Agent, or Firm*—Charles A. Huggett; Charles J. Speciale

[57] ABSTRACT

In the conversion of coal to gaseous and liquid products, the heat value of the coal is more completely retained by the products through the selective high efficiency conversion of coal to a low ratio syngas utilizing a portion of the Fischer-Tropsch generated heat recovered as steam, conversion of the low ratio syngas with a water gas shift F-T catalyst to a product comprising $C_1$ to $C_{50}$ hydrocarbons and oxygenates, converting the F-T product to premium gas and increased liquid fuels comprising gasoline and distillate with a special zeolite catalyst and recovering the SNG and LPG products of the selective steps to provide an improved product slate. A portion of the produced fuel gas is used in lieu of coal to provide some of the heat energy requirements of the combination process.

12 Claims, 1 Drawing Figure

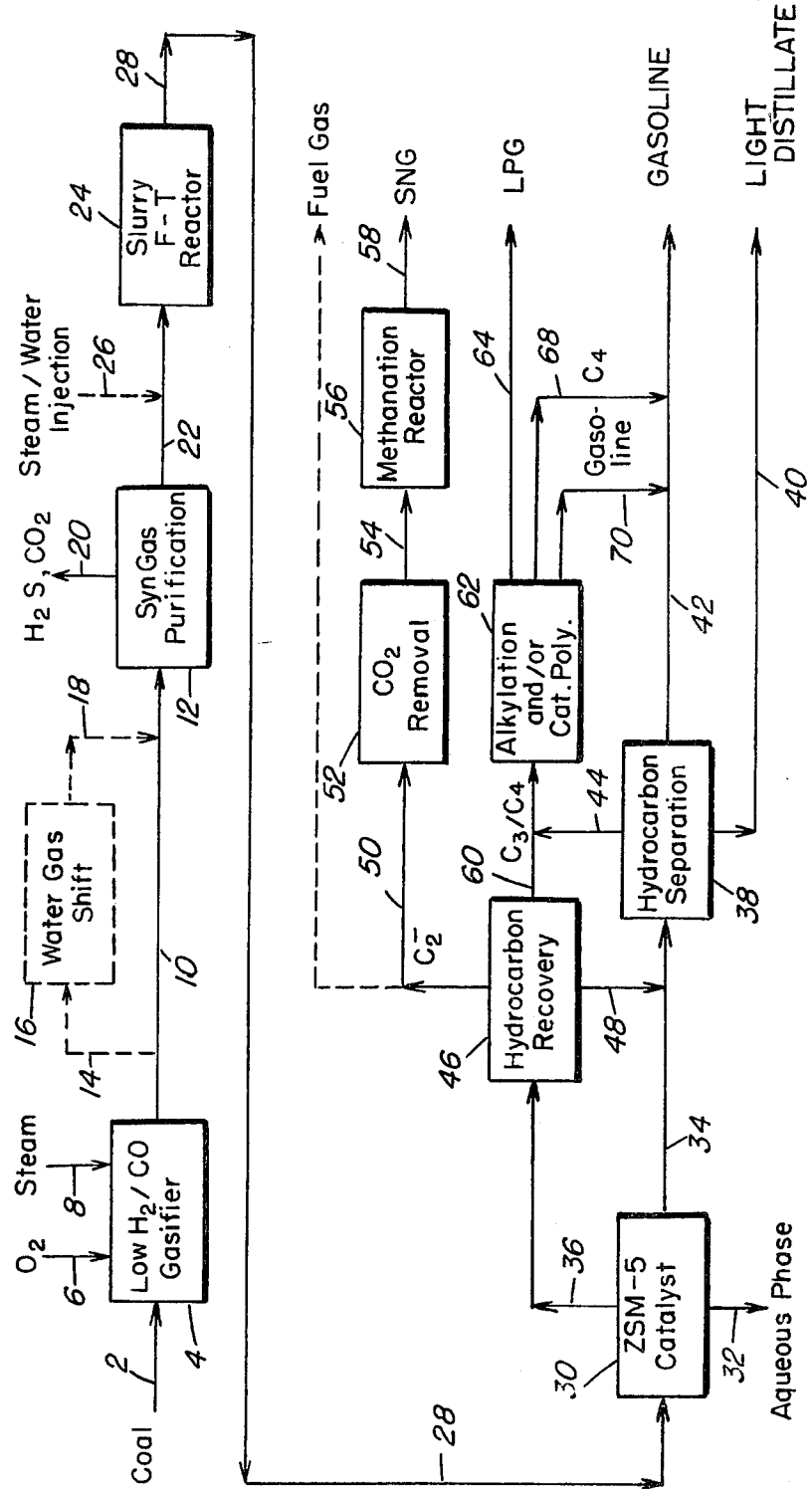

CONVERSION OF SYNTHESIS GAS TO HYDROCARBON MIXTURES UTILIZING DUAL REACTORS

BACKGROUND OF THE INVENTION

1. Field of the Invention

This invention is concerned with a combination process for converting synthesis gas, i.e. mixtures of gaseous carbon oxides with hydrogen or hydrogen donors, to hydrocarbon mixtures. In one aspect, the invention is concerned with a sequence of process steps for providing low ratio synthesis gas of less than 1 $H_2/CO$ ratio and conversion thereof to premium hydrocarbon fuels including distillates and gasoline boiling range hydrocarbons. The process of the invention is particularly concerned with processing low ratio $H_2/CO$ gases obtained from a coal gasification system of low cost and high fuel efficiency in a particular Fischer-Tropsch syngas conversion operation and catalytic upgrading of synthesis product to produce premium fuels.

2. Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. An excellent summary of the art of gas manufacture, including synthesis gas, from solid and liquid fuels, is given in *Encyclopedia of Chemical Technology*, Edited by Kirt-Othmer, Second Edition, Volume 10, pages 353–433 (1966), Interscience Publishers, New York, N.Y., the contents of which are herein incorporated by reference.

It is well known that synthesis gas comprising carbon monoxide and hydrogen will undergo conversion to form reduction products of carbon monoxide, at temperatures in the range of 300° F. to about 850° F. and pressures in the range of 1 to 1000 atmospheres, over a wide variety of catalysts. The Fischer-Tropsch process, for example, which has been extensively studied, produces a wide range of hydrocarbons, waxy materials, oxygenates and some liquid materials which have been successfully used as relatively low octane gasoline. The types of catalysts that have been studied for this and related processes include those based on metals or oxides or iron, cobalt, nickel, ruthenium, thorium, rhodium and osmium with and without promoters.

The range of catalysts and catalyst modifications disclosed in the art encompasses an equally wide range of conversion conditions for the reduction of carbon monoxide by hydrogen and provides considerable flexibility toward obtaining selected boiling range products. Nonetheless, in spite of this flexibility, it has not been possible heretofore to produce either olefin compositions comprising primarily internal double bond characteristics or aromatic hydrocarbons and boiling in the gasoline boiling range. A review of the status of this art is given in "Carbon Monoxide-Hydrogen Reactions", *Encyclopedia of Chemical Technology*, Edited by Kirk-Othmer, Second Edition, Volume 4, pages 446–488, Interscience Publishers, New York, N.Y.

Compositions of iron, cobalt or nickel deposited in the inner adsorption regions of crystalline zeolites are described in U.S. Pat. No. 3,013,990. Attempts to convert synthesis gas over X-zeolite base exchanged with iron, cobalt and nickel are described in Erdoel and Kohle-Erdgas, Petrochemie; Brennstoff-Chemie, Volume 25, No. 4, pages 187–188, April 1972.

One particularly desirable catalyst used in the conversion of syngas has been potassium promoted iron, which has been used in combination with special types of zeolites, such as ZSM-5, in order to produce valuable hydrocarbons. Thus, for example, copending application Ser. No. 934,140 filed Aug. 16, 1978 is directed towards the conversion of syngas with potassium promoted iron in admixture with HZSM-5. Although the process of this copending application is indeed effective in producing products having a substantial quantity of aromatics, nevertheless there are disadvantages associated with said process, primarily in the regeneration aspect of the catalyst. It is known that when processes of this type are operated under conditions which favor the production of aromatics, there are also produced substantial amounts of coke which are deposited about the acid ZSM-5 catalyst. This requires that the catalyst be subjected to frequent regeneration, and due to the fact that the process of said copending application Ser. No. 934,140 involved a catalyst mixture containing an iron catalyst and a ZSM-5 catalyst, the extent and amount of regeneration were limited by the effect that the regeneration would have on the iron component. Thus, although HZSM-5 by itself exhibits a remarkable stability with regard to regeneration of the same by burning off carbon deposits, the same is not true with respect to a Fischer-Tropsch catalyst in general and iron promoted potassium in particular.

In U.S. Pat. No. 4,086,262 issued Apr. 25, 1978, there is disclosed a process for the conversion of synthesis gas using a single stage process wherein the catalyst is a mixture of an iron containing Fischer-Tropsch catalyst and a ZSM-5 type zeolite. One of the examples, however, is directed towards a two bed operation wherein syngas is contacted over a first bed containing an iron catalyst and the total product is thereafter contacted in a second bed containing a ZSM-5 type zeolite. The example resulted in poor aromatic production and excessive methane production.

In U.S. Pat. No. 4,046,830 there is disclosed a process wherein the total effluent from a Fischer-Tropsch operation is upgraded after removal of catalyst fines over a ZSM-5 type zeolite. Although the process of said patent is indeed a valuable one, it has been found that it can be significantly improved upon by operating within more selective process conditions.

The upgrading of a product of Fischer-Tropsch synthesis has also been disclosed in the following U.S. patents which have been considered in the preparation of this application. These U.S. Pat. Nos. are 4,041,096; 4,044,063; 4,044,064; 4,046,829; 4,046,831; 4,079,741; 4,052,477; 4,053,532 and 4,071,574.

SUMMARY OF THE INVENTION

This invention is concerned with an improved combination process for obtaining premium fuels comprising gases, gasoline and higher boiling hydrocarbon distillates from coal. More particularly, the present invention is concerned with a combination process which more efficiently converts coal to premium gas and liquid products.

It has been found that a coal, coke or coal char gasifier with a low steam to oxygen ratio as well as low steam to coal ratio, such as provided by the British Gas Corporation-Lurgi slagging gasifier, has significant advantages in terms of thermal efficiency and cost and can lead to a reduction of up to 20-40% in syngas production costs. This advantage is larger for easier bituminous coal which has a lower reactivity. See Table 1 below.

TABLE 1

Lurgi Dry Ash Versus BGC-Lurgi Slagger

| Coal | Lurgi Dry Ash Western | Lurgi Dry Ash Eastern | BGC-Lurgi Slagger Frances (Scottish Non-caking Reactive) | BGC-Lurgi Slagger Eastern | BGC-Lurgi Slagger North Dakota Lignite |
|---|---|---|---|---|---|
| Gasifier Itself | | | | | |
| scf $O_2$/mscf Syngas | 135 | 187 | 168 | 157 | 189 |
| lb Steam/mscf Syngas | 46 | 75 | 10.6 | 8.6 | 9.1 |
| Steam/Oxygen | 7.5 | 8.5 | 1.3 | 1.15 | 1.0 |
| $H_2$/CO Ratio | 2.1 | 2.8 | 0.50 | 0.52 | 0.5 |
| Cold Gas Efficiency, % (adjusted for tars) | 80 | 76 | 89 | 90 | 91.0 |
| $CH_4$/CO + $H_2$ | 0.78 | 0.6 | 0.32 | 0.35 | 0.32 |
| Net Efficiency, % | 71 | 59 | 78 | 78 | 79 |
| Including Shift to Hydrogen to CO Ratio to 2 | | | | | |
| lb Steam/mscf Syngas (Total) | 46 | 75 | 40 | 39 | 39 |
| Net Efficiency, % | 71 | 59 | 71 | 70 | 71 |

However, a penalty is paid for this gain. The product gas of the slagging gasifier has an $H_2$/CO ratio of about 0.5 to 0.8 as compared to a ratio of about 2.0 produced by more costly gasifiers. The most advanced known Fischer-Tropsch process, practiced commercially at SASOL in South Africa, requires a synthesis gas with an $H_2$/CO ratio exceeding 2:1, produced in a Lurgi Dry Ash gasifier. If synthesis gas were produced in a more economical gasifier in a low $H_2$/CO ratio, it would require a shift conversion to increase its $H_2$/CO ratio to the level above 2:1 as required. Such shift reaction consumes a considerable amount of energy, especially in the form of steam, largely negating the high thermal efficiency of this gasifier. This is illustrated by the data in Table 1, which lists the steam requirements for shifting a low ratio $H_2$/CO gas to a high ratio of 2:1 as well as the reduction in thermal efficiency for the gas production. When using a western type coal (e.g. Frances), shifting to a ratio of 2:1 wipes out the advantage in thermal efficiency. In this operation, a slightly lower steam consumption requirement is offset by the higher oxygen consumption required by the operation. However, when using an eastern coal, the slagging gasifier with a subsequent shift of low ratio $H_2$/CO gas to 2:1 is still very significantly better than a prior art gasifier by Lurgi.

An efficient gasifier is identified as one having the characteristics of (a) using a low steam to dry, ash free coal weight ratio of less than 1.0 or a low ratio of steam to syngas produced of less than 30 lbs. steam per MSCF syngas, (b) producing a syngas with an $H_2$/CO ratio equal to or less than 1, (c) a low temperature of the gasifier exit gas of less than 2000° F.

Examples of gasifiers satisfying the above characteristics include slagging type gasifiers, such as the British Gas Corporation-Lurgi slagger or the Secord-Grate slagging gasifier or fluidized bed gasifiers such as the U-Gas and Westinghouse gasifiers. Data for the BGC-Lurgi slagging gasifier have been used in the illustrative examples presented below. The Texaco gasifier of Table 2 below has an exit gas temperature in excess of 2000° F., and the Lurgi Dry Ash gasifier requires using a large amount of steam.

The thermal efficiency of a gasifier may be defined as:

Net Efficiency =
$$1 - \frac{\text{(All Energy Input - All Energy Output - Impurity } LHV)}{\text{(Net Coal } LHV)}$$

LHV = Low Heating Value

Net Coal LHV = LHV coal – LHV (Char + Tar + Phenol)

Energy Input includes energy used in preparing oxygen and steam

Energy Input and Output are in fuel LHV basis

Impurity LHV = LHV ($H_2S$ + COS + $NH_3$)

To fully utilize the lower cost slagging type of gasifier, a process is required that can convert the low ratio ($H_2$/CO) syngas directly to higher carbon chain products. A specially arranged and operated Fischer-Tropsch process can achieve an internal shift in the following manner with the proper catalyst:

The water formed by the reaction, $$CO + 2H_2 \rightarrow CH_2 + H_2O \qquad (1)$$

reacts with CO to give $H_2$ and $CO_2$ leading to the net reaction, $$2CO + H_2 \rightarrow CH_2 + CO_2 \qquad (2)$$

which requires an $H_2$/CO ratio of 0.5. Thus, any gas with an $H_2$/CO ratio >0.5 can be converted efficiently in high yields. This ratio can be lowered, to about 0.4, by injecting water together with the syngas. The low $H_2$/CO ratio syngas can be used to advantage in the Fischer-Tropsch operation. It reduces methane production and improves gasoline yield when compared to the prior art process which operates at an $H_2$/CO ratio of >2:1. The disadvantage of the low $H_2$/CO ratio syngas is that it very readily leads to carbon formation according to the Boudouard reaction:

$$2CO \rightarrow C + CO_2$$

which can be minimized only by very close temperature control of the highly exothermic reaction. One process known to applicants which has demonstrated the ability to work with a low $H_2/CO$ ratio syngas is a slurried catalyst Fischer-Tropsch process utilized by Rheinpreussen A. G., which operated a pilot plant with a capacity of about 8 barrels of gasoline per day using a feed gas with an $H_2/CO$ ratio of about 0.7:1. The product of this process is highly olefinic and contains oxygenated compounds including alcohols and acids and requires further upgrading.

The processing concepts of the present invention were developed in substantial measure by the following analysis. An approximate thermal efficiency of various process combinations was developed as provided in Tables 2 and 3.

Separated $C_2=$ to $C_4=$ olefins are either used for alkylation of isobutane or polymerized. $C_3+$ or $C_4+$ hydrocarbons are recovered; the lighter, gaseous products can be directly used as medium BTU gas, after removal of a portion of the $CO_2$ if necessary. The light gaseous products can also be converted to a high BTU SNG by known processes.

In Case 5, Case 4 was modified to increase the liquid yield at a slight sacrifice in thermal efficiency. In this case (5), the light gaseous products containing $H_2$, CO and $C_1+C_2$ hydrocarbons are cryogenically separated and the syngas is recycled to the Fischer-Tropsch process. Part of the $C_2-$ fraction is also used as plant fuel.

The high thermal efficiency (70%) with which coal is

TABLE 2

| % of LHV Coal Feed | PRODUCT SELECTIVITY (% OF LHV OF COAL) | | | | |
|---|---|---|---|---|---|
| | Case 1<br>D.A. Lurgi<br>Methanation | Case 2<br>Dry Ash Lurgi/SASOL<br>Fischer-Tropsch/<br>Refining | Case 3<br>Texaco/<br>Slurry FT/<br>Zeolite | Case 4<br>BGC-Lurgi<br>Slagger/<br>Slurry FT/<br>Zeolite | Case 5<br>BGC-Lurgi<br>Slagger/<br>Slurry FT/<br>Zeolite |
| SNG | 64 | 35 | 9 | 28 | 15 |
| Gasoline | — | 14 | 44 | 36 | 45 |
| Diesel and Fuel Oil | — | 3 | — | — | — |
| LPG | — | 1 | 4 | 6 | 7.0 |
| Alcohols | — | 1 | — | — | — |
| % Thermal Efficiency (LHV) | 64 | 54 | 57 | 70 | 67 |
| Liquid Products | | | | | |
| (BBL/Ton DAF Coal) | 0 | 0.96 | 2.48 | 2.03 | 2.65 |
| Gasoline | | | | | |
| (BBL/Ton DAF Coal) | | 0.73 | 2.26 | 1.85 | 2.31 |

TABLE 3

| Product Distribution in Percent of Product LHV | | |
|---|---|---|
| | Case 2<br>DRY ASH<br>LURGI/<br>SASOL<br>TYPE F. T. | Case 4<br>BGC-LURGI<br>SLAGGER/<br>SLURRY<br>FT/MOBIL |
| Methane in syngas | 44 | 25 |
| SNG formed in conversion process | 12 | 8 |
| Methane from methanating unconverted syngas | 8 | 7 |
| Total SNG, % | 64 | 40 |
| Alcohols, % | 2 | — |
| LPG, % | 2 | 9 |
| Diesel and fuel oil, % | 6 | — |
| Gasoline, % | 26 | 51 |
| | 100 | 100 |

In Table 2, determined thermal efficiencies and product distributions are given for the different gasifiers identified in Table 1, coupled with different downstream conversion processes.

Case 1 is based on a study which developed data for producing syngas from western coal followed by methanation. The second case (Case 2) is also developed from the Case 1 study with coproduction of gasoline and LPG/SNG via prior art Fischer-Tropsch synthesis and product refining, using a D. A. Lurgi gasifier. Case 3 and Case 4 are based on data and estimates made for Texaco and the slagging gasifier respectively.

In Case 4, the gas from the slagging gasifier is shifted to an $H_2/CO$ ratio of 0.7 and converted in a liquid-catalyst slurry Fischer-Tropsch reactor operation.

The products of the liquid-catalyst slurry Fischer-Tropsch operation are thereafter directly passed into a second stage reactor containing a ZSM-5 zeolite catalyst followed by a hydrocarbon product recovery plant.

converted to clean premium fuels including >40% gasoline+diesel fuel in Case 4 of Table 3 is a result of several unique features which originate in the specific combination of conversion processes of this invention. A large part derives from the use of a thermally efficient gasifier (slagger) as mentioned above; additional savings in energy are provided by utilizing the low $H_2/CO$ syngas directly in the Fischer-Tropsch reactor with little or no outside shift conversion which would require large amounts of steam; thirdly, the Fischer-Tropsch reactor operates at about the same pressure as the gasifier (150–400 psi) and thus requires very little, if any, compression; fourthly, it has been found that the use of a particular Fischer-Tropsch conversion process provides additional savings of energy when coupled with the slagging gasifier. This fourth contributing factor derives from the use of a liquid phase-suspended catalyst therein or slurry Fischer-Tropsch reaction system operated without recycle. In this operation, the heat of reaction can be recovered with exceptionally high efficiency in the range of about 60–85% in the form of medium pressure steam. Other types of Fischer-Tropsch reactors, such as fixed bed reactors of the ARGE type, require considerable gas recycle to control the reaction temperature and reject the heat of reaction at lower temperature with much lower efficiency of heat recovery. We have found that the large amount of heat recovered from the slurry Fischer-Tropsch reactor can be used in the gasifier, especially the associated oxygen plant, with high efficiency only in combination with a slagging gasifier, but not in combination with other gasifiers such as the Texaco gasifier, since the latter already produces an excess of steam. These factors in their totality and specific combination are responsible for the exceptionally high efficiency and product yield of the present invention (Case 4), which is by far better than any existing or realistically projected process for producing high grade fuels from coal.

As shown in Table 2, the higher thermal efficiency and hence higher yield of clean premium fuels of the present invention (Case 4-5) over alternative process combinations (Case 1-3) is clearly apparent. Case 1, while having moderately high efficiency, produces only SNG, i.e. gaseous methane, which is not as desirable as liquid automotive fuels. Case 3 utilizes a modern gasifier presently under development, the Texaco gasifier; while it produces a high yield of liquid products, it has a lower overall thermal efficiency and lower yield of total clean fuel products than Case 4. In particular, the great advantage of Case 4 over the best prior art Technology (Case 2) is clearly illustrated in Table 2. Not only is the coal converted in a higher yield to clean fuels (70% vs. 54%), but the proportion of the more valuable liquid products, gasoline, is considerably increased (from 26% to 51% of the products), as shown in Table 3.

In general, it is found that the present process combination provides a product distribution in which at least 35% and preferably at least 40% of the total products (measured in LHV—low heat value) are liquid premium products, i.e. gasoline and diesel/fuel oil. For comparison, the thermal efficiency determined for producing methane from western coal is about 64%; less than 60% for producing methane from eastern coal; 50-55% for producing gasoline from a process known as H-Coal or a donor solvent process; and 70-75% for producing solvent refined coal (SRC) which is a low quality product.

The processing combination of this invention more particularly defined below provides high selectivity for high grade fuel comprising methane, LPG, gasoline and distillate and the amount of high grade fuel produced per pound of coal is high due to the high thermal efficiency of the combination operation.

The slurried catalyst or catalyst suspended in a liquid phase Fischer-Tropsch process requires little, if any, compression, generates medium pressure saturated steam which is used in the syngas producing plant and permits the highest recovery of exothermic heat for steam generation. It, therefore, receives a substantial investment and energy credit for this high steam generation capability. It is this difference in the steam generation and utilization synergism which gives the slagger/slurried catalyst Fischer-Tropsch process route its advantage over other combination conversion routes.

If the product of a liquid fuels producing operation has a C/H ratio characteristic of $(CH_2)_n$, a syngas conversion process that makes use of internal shift can efficiently use a feed gas with an $H_2/CO$ ratio as low as 0.50. If a higher $H_2/CO$ ratio syngas is desired, a gasifier is needed that includes internal or downstream water gas shift and requiring steam for the purpose. A low $H_2/CO$ ratio gas is relatively free of $CO_2$ or contains very little $CO_2$ and the absence of $CO_2$ makes it easier to remove $H_2S$ by the known Claus process.

A coal or char gasifier producing low ratio $H_2/CO$ syngas requires less investment than that to produce high $H_2/CO$ ratio syngas because of the large steam and oxygen requirements for high ratio gas. Because of these large and significant differences in investment and energy requirements in preparing steam and oxygen, the relative amounts of these reactants required in a char or coal gasification operation have an important bearing on the thermal efficiency of the process. That is, the highest efficiency occurs at the lowest steam to oxygen ratio that satisfies the stoichiometry for an $H_2/CO$ ratio gas of about 0.50 and the operating temperature constraints of the operation. It may be said that the generation of steam used in a gasifier is equivalent to using oxygen instead of air to combust coal and is therefore more expensive and less efficient.

The extensive study contributing to the concepts of the invention herein identified shows that an advantage in coal or char gasification efficiency can be achieved by operating at low steam and oxygen ratios. It was also found that variations in gasifier design and coal properties can change the efficiencies obtained but they always are best in the regions of low steam and oxygen ratios. It was observed that steam consumption increases monotonically as steam to oxygen ratios increase. On the other hand, oxygen consumption remains almost constant. Thus, operating to produce high $H_2/CO$ ratio syngas increases the steam requirements without effecting savings in oxygen consumption.

For a given gasifier, the amount of syngas produced per pound of dry, ash-free coal increases with the steam to oxygen ratio used. However, an increase in gas production cannot be used to offset the decrease in net efficiency obtained on increasing the steam to oxygen ratio, as energy from either coal or fuel gas is required to raise the additional steam. Thus, to obtain high efficiencies in the gasification step, the $H_2/CO$ ratio produced must be kept low, below about 1/1 ratio and preferably in the range of 0.4 to 0.8. This constraint in gas production requires a syngas conversion operation which can utilize the produced low ratio syngas under relatively economic conditions and long on-stream catalyst life in order that the combination process can benefit from the higher thermal efficiency of the gasifier as herein identified. The combination process of this invention has particular merit when it is desired to produce premium fuels comprising gaseous hydrocarbons, gasoline boiling hydrocarbons, distillates or a combination thereof.

For gasifiers that are coupled to syngas conversion processes, there is an advantage to raising cold syngas efficiency relative to net efficiency. The percent cold syngas efficiency is defined as (syngas LHV/net coal LHV to gasifier)×100. Syngas processes generate steam that can be used to satisfy that steam requirements of the gasifier and to prepare oxygen for use in the gasifier, thereby obtaining a gain in overall operating efficiency. In addition, the gasifier efficiency can be improved by producing countercurrent flow of coal to steam and oxygen. A low exit temperature is desirable to minimize the amount of heat that has to be supplied to the gasifier for combustion. In addition, a low exit temperature is desirable for the syngas conversion process, since the syngas conversion process generates both excess steam as well as some off-gases that can be used for power generation or other purposes.

It has also been discovered by this development that premium fuels comprising aromatic and/or olefinic gasoline of enhanced octane number and low pour distillates can be produced economically and in high yields by the processing combination of this invention. That is, a low ratio syngas mixture comprising an $H_2/CO$ ratio equal to and more usually less than 1 as obtained from a low cost coal gasifier and absent high cost external facilities for effecting water gas shift reactions can be reacted in one or more sequential or parallel reactors with a Fischer-Tropsch catalyst comprising water gas shift characteristics suspended or slurried in a liquid medium and maintained under selected operating reaction conditions including a temperature less than 600° F. The synthetic hydrocarbon product comprising oxygenates obtained from this suspended catalyst in a liquid phase Fischer-Tropsch operation also referred to as a slurried Fischer-Tropsch catalyst conversion operation, with or without any separation of product to remove oxygenates, or light and heavy hydrocarbons from naphtha, is thereafter processed in one or more sequentially arranged reactors at a temperature in the range of 550° to 850° F. and a pressure of less than 700 psig by contact with a special zeolite catalyst. The special zeolite catalyst is preferably a ZSM-5 zeolite of desired acidity and selectively characteristics to obtain an improved naphtha and/or distillate conversion product thereof wherein the methane plus ethane yields are maintained desirably low and the $C_5^+$ gasoline fraction and/or higher boiling distillate material are obtained in substantially improved yield. The gasoline fraction preferably has a boiling point of less than 400° F. at its 90% overhead.

The process combination of this invention allows for considerably greater flexibility in product distribution obtained by adjustment of reaction conditions in the Fischer-Tropsch operation, the zeolite catalyst conversion operation and thus the catalyst on-stream life of each operation is improved. Since separate reactors are used and each reactor can be operated at substantially optimum conditions, each catalyst employed can be regenerated separately as required so that the process is capable of being operated at long on-stream cycle times before catalyst regeneration is required.

In the novel process combination of this invention, the slurried Fischer-Tropsch catalyst is operable for long on-stream times, since the operation minimizes the deposition of coke on the catalyst and does not promote the oxidation of some catalyst particles to the exclusion of others. On the other hand, the zeolite catalyst can be used in either a fixed or fluid catalyst bed system under operating conditions particularly suitable for producing high octane gasoline or premium light distillates and the zeolite catalyst is remarkably stable during many regeneration cycles. It is known that the regeneration conditions for an iron Fischer-Tropsch catalyst are different from those necessary to regenerate an acidic zeolite catalyst and this is true particularly for the special zeolite catalyst used in the process of this invention.

The processing sequence of the present invention is a particularly novel combination of high processing efficiency for the reasons herein presented for converting syngas to high yields of premium hydrocarbons including gasoline boiling range product and/or distillates. Of particular significance is the finding and realization that the low ratio syngas ($H_2/CO = 1/1$ or less) is not detrimentally critical to this process, and utilization of a Fischer-Tropsch catalyst containing or provided with water gas shift characteristics in the slurried catalyst reactor system can be relied upon for effecting high conversions of $H_2$ and CO when processing both low and higher ratio syngas feed. The importance of the processing combination becomes even more interesting when it is recognized that a low cost syngas generation operation can be taken advantage of in contributing to the overall economics of the process by maximizing the recovery of heat from the exothermic reaction by steam generation and utilizing steam thus generated by the Fischer-Tropsch slurry operation for generating reactants for the syngas generation operation. That is, it is much less costly to generate a low $H_2/CO$ syngas, 1/1 or less, than it is to generate a higher ratio syngas. Furthermore, a low ratio syngas in the range of 0.4 to 0.7 can be adjusted by the water gas shift activity of a Fischer-Tropsch catalyst on a once-through basis to provide high yields of $C_3$ plus hydrocarbons and oxygenates. The reaction mechanisms by which hydrocarbons are formed from syngas over different catalyst compositions have been studied and reported on by many researchers in the field.

It was technically exhilarating to develop and recognize the high thermal efficiency of the combination process of this invention when an economically produced low ratio $H_2/CO$ syngas obtained by using by-product high temperature steam of a special Fischer-Tropsch synthesis operation is thereafter converted in said special Fischer-Tropsch operation to high yields of hydrocarbons and oxygenates using a Fischer-Tropsch catalyst component comprising water gas shift characteristics and thereafter effecting conversion of the Fischer-Tropsch products obtained with a special zeolite conversion catalyst to high quality premium products in significant yields.

Thus, the process combination of the invention is not one of idle curiosity or a mere add-on of known processes, but one found to be a highly efficient and economic process for producing premium fuels from coal. Furthermore, the heating value of products represents a larger portion of the heating value of the coal charged to the combination.

The processing sequence of this invention adapts some known technology of suspended Fischer-Tropsch synthesis catalyst in a liquid medium to a relatively new and low cost syngas generation technology from coal in a mutually compatible relationship contributing to improving the operation of each step in a realistic synergistic relationship between the process steps. The products of the individual steps and from the combination of steps are recovered and converted in the sequence of steps to recover selected premium fuels in higher yields with greater overall energy savings for the combination of steps.

The potential impact of various gasifiers on the overall economics of indirect coal liquefaction, that is conversion of coal to syngas ($H_2 + CO$) and conversion of the formed syngas with a Fischer-Tropsch catalyst to hydrocarbon products, has been evaluated. The heretofore known coal gasifiers and associated offsite facilities involved in such syngas production represent a large part, up to about 70% if not more, of the costs for converting coal to hydrocarbon fuels. The high thermal energy requirements of the gasification step to produce the high ratio $H_2/CO$ gas ($>1:1$) impacts very strongly on the overall thermal efficiency of the operation. The results of an extensive study leading to the correlation and the development of the particular combination process of this invention clearly indicated that gasifiers requiring low steam to oxygen ratios and thus producing no more and more usually less than about 1/1 hydrogen to CO ratio syngas have certain inherent thermal efficiency advantages, provided high temperature low cost steam is available and provided off-site water gas shift facilities are minimized or eliminated. That is, a combination process using a gasifier producing a low ratio syngas (1/1 or less of $H_2/CO$) that is more economical to produce than ever achieved before, which gas is thereafter directly and selectively converted to hydrocarbons in the range of $C_1$ to $C_{50}$ hydrocarbons with particular preference for gasoline and higher boiling hydrocarbons, is found to have significant cost advantages over other routes for coal conversion to gasoline. Low $H_2/CO$ ratio syngas can be converted in a slurry type of reaction system wherein the Fischer-Tropsch catalyst is suspended at least partially in a liquid medium compatible with the reaction temperatures encountered and product produced without encountering the difficulties identified with other types of reaction systems including fixed bed and fluidized catalyst systems. When processing a low ratio syngas to gasoline boiling range products at high temperature, considerable carbon formation deposits on the catalyst in fixed and fluid bed systems where a less stringent catalyst particle temperature variation exists. In the liquid catalyst slurry system, the catalyst particle surface temperature is more closely controlled and thus better results are obtained than obtained particularly in fixed catalyst arrangements.

A low cost gasifier now under development is known as the slagger gasifier developed by British Gas Corporation and Lurgi.

The slurried catalyst reactor system or otherwise identified as a suspended Fischer-Tropsch catalyst in a liquid medium suitable for the purpose of converting syngas to hydrocarbon products has been the subject of numerous patents. Early patents on the subject are U.S. Pat. Nos. 2,438,029; 2,680,126; 2,775,607; 2,852,350 and numerous others. The slurried Fischer-Tropsch catalyst system of this invention is distinguishable from the prior art in many respects as herein identified.

In the particular environment of this invention directed to converting relatively low ratio syngas (1/1 or less $H_2/CO$ ratio), it is essential that the CO reducing catalyst used include water gas shift activity or characteristics so that steam formed in the Fischer-Tropsch operation by converting the low ratio syngas will react with charged CO to form $H_2$. Examples of CO reducing catalysts comprising shift activity are iron alone, or iron, cobalt, ruthenium provided with an added shift catalyst component. Shift catalysts suitable for the purpose include those containing the elements Fe, Cr, Zn or Cu. It is also contemplated charging some steam with syngas of 0.7 $H_2/CO$ ratio or less.

It is important for temperature control in the slurried catalyst Fischer-Tropsch operation to maintain sufficient heat exchange fluid generally comprising a relatively high boiling portion of the synthesis hydrocarbon product in direct contact with the catalyst particles to substantially suspend the particles and maintain predetermined and desired temperature control and thus limit the build-up of coke on the catalyst particles. Thus it is possible in the liquid phase Fischer-Tropsch operation to more closely restrict the temperature exotherm about any given particle within more narrow limits, to use more selective operating temperatures, and achieve results not obtainable in a fixed bed catalyst system. The level of liquid in the slurry reaction zone is maintained at desired level by the continuous withdrawal of vaporous and liquid product with and without suspended catalyst. The recycle of a liquid product with catalyst particles concentrated therein to the reaction zone following temperature adjustment is pursued as required.

A product of the Fischer-Tropsch synthesis operation separated from catalyst particles, absence that required for recycle to maintain the desired liquid phase, is recovered for further processing as herein provided. This recovered material comprising liquid and gaseous components of the Fischer-Tropsch operation may be separated to recover oxygenates and $C_4$ minus gaseous components therefrom for treatment separately from $C_5^+$ hydrocarbons, or a total product mixture thereof without separation is passed in contact with a separate bed of the special zeolite catalyst herein identified and particularly represented by ZSM-5 zeolite. The special zeolite catalyst is maintained under particularly desired activity and selectivity conditions to convert ethylene, $C_3^+$ or $C_5^+$ hydrocarbons with and without oxygenates either separately or together to hydrocarbon products including higher octane gasoline boiling range products and/or distillate fuels.

Crystalline Aluminosilicate Zeolites

The crystalline aluminosilicate zeolites utilized herein are numbers of a novel class of zeolites that exhibits unusual properties. Although these zeolites have unusually low alumina contents, i.e. high silica to alumina ratios, they are very active even when the silica to alumina ratio exceeds 30. The activity is surprising, since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to large molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (C.I.) values for some typical crystalline aluminosilicates (CAS) are:

| CAS | C.I. |
| --- | --- |
| ZSM-5 | 8.3 |
| ZSM-11 | 8.7 |
| ZSM-12 | 2 |
| ZSM-35 | 4.5 |
| ZSM-38 | 2 |
| TMA Offretite | 3.7 |
| Beta | 0.6 |
| ZSM-4 | 0.5 |
| H-Zeolon (Mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for 1 hour, for example, followed by base exchange with ammonium salts, followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts, followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combination. Natural minerals which may also be treated include ferrierite, brewsterite, stilbite, dachiardite, epistilbite, heulandite, and clinoptilolite. The preferred crystalline aluminosilicates are ZSM-5, ZSM-11, ZSM-12, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites are associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, −11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5% by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely, with the zeolite content ranging from between about 1 to about 99% by weight and more usually in the range of about 5 to about 80% by weight of the dry composite.

The low $H_2CO$ ratio syngas, 0.5 to 1 and more usually in the range of 0.5 to about 0.8 obtained as herein defined, is converted in the slurried catalyst Fischer-Tropsch reactor operation at a temperature within the range of 400° F. up to about 600° F. and a pressure within the range of 50 to 700 psig. The contact time of the syngas is chosen to provide high conversion per pass, at least 50%, preferably 70 to 95%. This value depends on the length of reactor, the nature of the Fischer-Tropsch catalyst and its concentration in the slurry. The preferred catalyst is a precipitated iron oxide that has been calcined and pretreated with CO and $H_2$ gas. A space velocity between about 1 liter and 10 liters of syngas (STP) per gram iron per hour will provide the desired high conversion. Within these operating parameters, the temperature exotherm encountered about any given suspended catalyst particle in the liquid phase material is closely retained within narrow limits, thereby contributing to a more satisfactory operation of the system for producing desired liquid products. The suspended catalyst particles retained in the liquid phase may be selected from within the range of about 1 to 50 microns, thereby providing a larger amount of surface-active sites than obtainable with larger sized catalyst particles or extrudate used in fluid and fixed catalyst bed systems. The low temperature operation contemplated is particularly desirable for reducing the production of $C_1$ and $C_2$ hydrocarbons, for reducing carbon build-up on the catalyst and for improving selectivity of the operation for producing liquid hydrocarbon. Thus, not only is the liquid product selectivity maintained high by the low temperature liquid slurry Fischer-Tropsch operation, but more importantly the low cost gasifier which reduces gasification costs from 20 to 40% can be used to advantage with the slurried Fischer-Tropsch catalyst operation. Whether or not the liquid product is generally heavier than that obtained from a higher fixed catalyst bed operation or a fluid catalyst bed operation or whether there are more or less oxygenates formed is not material, since the downstream special zeolite catalyst conversion operation effected in one or more catalyst beds in one or more separate reaction zones can be relied upon to convert the oxygenates to hydrocarbon products, hydrodewax hydrocarbons boiling above the gasoline boiling range, and improve the octane of hydrocarbons in the gasoline boiling range recovered from the Fischer-Tropsch operation.

The processing combination of this invention is open to numerous variations on the general combination sequence of low cost gasifier, slurried Fischer-Tropsch catalyst conversion operations and special zeolite catalyst conversion of products obtained from the Fischer-Tropsch operation. That is, there is a preferable combination of the special zeolite catalyst reactors such as in a parallel arrangement so that one reactor may be undergoing catalyst regeneration while one or more other separate reactors are being used to process hydrocarbon and oxygenates separately or together. On the other hand, a liquid Fischer-Tropsch fraction comprising hydrocarbons and some oxygenates, if not all oxygenates, may be separated into a gasoline boiling range fraction and a higher boiling range fraction so that each may be separately processed under more desired and selective conditions leading to the production of high octane gasoline, dewaxed light oil material and a hydrocarbon product of converted oxygenates.

In the two stage synthesis gas conversion operation of Examples 1 and 2, a liquid phase slurry type Fischer-Tropsch catalyst synthesis operation was conducted in a stirred-tank reactor with low ratio $H_2/CO$ syngas, and the total effluent from the Fischer-Tropsch reactor operation was upgraded in a fixed catalyst bed operation in a second reactor containing HZSM-5 crystalline zeolite.

EXAMPLE 1

Three grams of a co-precipitated iron-potassium-copper catalyst (0.6 wt.% each of $K_2CO_3$ and Cu based on metallic iron) and 150 ml of a synthetic paraffinic oil (a lube oil base stock) were placed in a 300 ml stainless steel autoclave (the first reactor), equipped with a stirrer which was operated at 900 rpm. One gram of steamed HZSM-5 ($\alpha=70$) was placed in a fixed bed reactor (the second reactor). Then the whole system was purged with nitrogen while the temperatures were brought up to 482° F. and 673° F. for the first and the second reactors, respectively. At that time, syngas with an $H_2/CO$ ratio of 0.65 was fed at atmospheric pressure into the first reactor at 193 ml/min (at 24° C. and 1 atmosphere) and the temperature of the second reactor was adjusted to 572° F. and held at that temperature for 1½ hours.

After the above pretreatment of the Fischer-Tropsch catalyst, the pressure was raised to 200 psig and the operating conditions adjusted. The operating conditions and detailed product distribution are given in Table 4. Total syngas conversion was 79% and methane in hydrocarbon was only 6.7 wt.%. The $C_5^+$ selectivity (in hydrocarbon) and aromatics in $C_5^+$ were 61.6 wt.% and 27.6 wt.% respectively. In addition, the $C_5^+$ liquid produced was essentially in the gasoline range (376° F. at 90% overhead). The results demonstrate that the two stage process using a low ratio $H_2/CO$ syngas feed produces a high yield of high quality gasoline.

EXAMPLE 2

The two stage syngas conversion of this example was conducted in the same manner as in Example 1 under the same operating conditions except that the space velocity was reduced to 2.9 liters of syngas (at 24° C. and 1 atmosphere) per hour per gram of iron. The results obtained are compiled in Table 4. High total syngas conversion (89%) with low methane production was obtained. In this operation, a higher yield of aromatics was obtained in the $C_5^+$ product and the gasoline 90% overhead was 380° F.

TABLE 4

| Two Stage Syngas Conversion at 200 Psig | | |
|---|---|---|
| | Ex. 1 | Ex. 2 |
| $H_2/CO$ | 0.65 | 0.65 |
| Temp., 1st Reactor | 509° F. | 509° F. |
| 2nd Reactor | 673° F. | 672° F. |
| WHSV, 1st Reactor | 2.8 | 1.4 |
| 2nd Reactor | 8.5 | 4.2 |
| GHSV, 1st Reactor, 1/hr/g Fe | 5.8 | 2.9 |
| Conversion, wt. % | | |
| CO | 78 | 91 |
| $H_2$ | 80 | 87 |
| Total Syngas | 79 | 89 |
| Total Effluent, wt. % | | |
| Hydrocarbon | 17.0 | 19.5 |
| $H_2$ | 1.0 | 0.6 |
| CO | 19.6 | 9.0 |
| $CO_2$ | 61.2 | 69.9 |
| $H_2O$ | 1.2 | 1.0 |
| Hydrocarbon Dist., wt. % | | |
| $C_1$ | 6.7 | 8.5 |
| $C_2°$ | 4.4 | 6.2 |
| $C_2=$ | 0.9 | 0.5 |
| $C_3°$ | 5.7 | 8.2 |
| $C_3=$ | 2.7 | 1.3 |
| $i-C_4$ | 7.7 | 8.2 |
| $n-C_4$ | 5.5 | 7.2 |
| $C_4=$ | 4.7 | 2.0 |
| $i-C_5$ | 6.5 | 6.6 |
| $n-C_5$ | 4.6 | 5.1 |
| $C_6^+$ non-aromatics | 33.6 | 27.0 |
| Aromatics | 17.0 | 19.2 |
| | 100 | 100 |
| $C_1+C_2$ in H.C., wt. % | 11.1 | 15.2 |
| $C_3+C_4$ in H.C., wt. % | 27.3 | 26.9 |
| $C_5^+$ in H.C., wt. % | 61.6 | 57.9 |
| Aromatics in $C_5^+$, wt. % | 27.6 | 33.2 |
| Octane (R+O) of Liquid Product | 89 | — |
| Boiling Range of Liquid Product (90% Overhead) | 371° F. | 353° F. |

FIG. 1 is a sketch of the processing combination of this invention in block flow arrangement, including one arrangement for separating and heating the product obtained from the special zeolite catalyst conversion operation.

In the arrangement of FIG. 1, presented by way of example, coal is charged by line 2 to a low cost gasifier 4 producing low ratio $H_2/CO$ gas as above discussed. Oxygen is charged to the gasifier by line 6 and steam by line 8. A low ratio $H_2/CO$ gas generally about 0.5

$H_2/CO$ ratio or up to about 0.7 depending upon the operation is recovered by line 10 and passed to a syngas purification operation 12. All or a portion of the syngas recovered from gasifier 4 may be passed by line 14 to a shift reactor 16 and thence by line 18 to purifier 12. In shift reactor 16, the low ratio syngas of about 0.5 or more $H_2/CO$ ratio may be adjusted to a higher value in the range of about 0.6 to about 1.0. In purification zone 12, hydrogen sulfide is separated from the syngas and removed by line 20. In addition, some $CO_2$ is removed in this operation and may be removed by line 20 or by a separate line.

The purified syngas is passed from purifier 12 by line 22 to the liquid phase-suspended Fischer-Tropsch catalyst operation 24 particularly desired by this invention and discussed above. Steam or water may be added by line 26 to the syngas passed to the Fischer-Tropsch operation in zone 24. The liquid phase operating conditions of zone 24 coincide with those discussed above and are selected to particularly produce gasoline and distillate boiling range material.

In the arrangement of FIG. 1, all of the product of the Fischer-Tropsch operation is shown being passed by line 28 to the special zeolite catalyst (ZSM-5) conversion operation discussed above. Of course, as identified above, the Fischer-Tropsch product may be separated so that different components of the Fischer-Tropsch product may be separately processed over the zeolite catalyst in more than one reaction zone to more particularly optimize the conversion of the feed charged thereto.

In the particular embodiment of FIG. 1, the total Fischer-Tropsch product is charged to reaction zone 30 comprising the special zeolite catalyst (ZSM-5) maintained under the conversion conditions identified above to produce premium fuels. In zone 30, a separation is also made which permits the recovery of a water phase withdrawn by line 32, a liquid hydrocarbon phase withdrawn by line 34 and a light gas phase withdrawn by line 36. The hydrocarbon phase in line 34 is passed to a hydrocarbon separation zone 38 wherein a separation is made to recover light distillate withdrawn by line 40, a gasoline fraction withdrawn by line 42 and a gas phase withdrawn by line 44.

The light gas stream in line 36 is passed to a hydrocarbon recovery zone 46 wherein a separation is made to recover liquid material withdrawn by line 48 for passage to separation zone 38, $C_2$ minus material withdrawn by line 50. The light material in line 50 may be used as fuel gas or it may be passed to a $CO_2$ removal zone 52 and thence by line 54 to a methanation reactor 56 for the production of SNG removed by line 58.

A gaseous stream comprising $C_3$–$C_4$ hydrocarbons is withdrawn from zone 46 by line 60 and passed to zone 62 where one or both of alkylation and catalytic polymerization are effected to produce more desirable products. An LPG product is withdrawn by line 64, $C_4$ hydrocarbons for blending are withdrawn by line 48 and gasoline boiling range material product of the reactions effected in zone 62 are formed by line 70 for blending with gasoline product in line 42.

It will be recognized by those skilled in the art that numerous variations may be made upon the processing arrangement above briefly discussed without departing from the spirit and scope of the present invention. This of necessity will occur when processing the Fischer-Tropsch product comprising gaseous hydrocarbons, liquid hydrocarbons in the gasoline boiling range, distillate boiling hydrocarbons and separated oxygenates in separate contact zones with the special zeolite catalysts herein identified. When processing separately, it is contemplated combining the products of the separate operations to recover SNG, LPG, high octane gasoline and light distillate products.

We claim:

1. In a processing combination comprising the steps of coal gasification to produce $H_2$ and CO, F-T hydrocarbon synthesis from said $H_2$ and CO and upgrading the product of F-T synthesis to produce more desirable gaseous hydrocarbon products, gasoline and distillate material wherein said coal gasification is carried out in a gasifier characterized by:
   (1) being capable of producing syngas with less than 30 lbs. of steam per MSCF of syngas,
   (2) producing a low ratio syngas with a $H_2/CO$ ratio of 0.4 to 1, and
   (3) a gasifier exit gas temperature of less than 2000° F., the improvement which comprises:

charging said low ratio $H_2/CO$ syngas to an F-T syngas conversion zone comprising a catalyst providing water gas shift and CO reducing characteristics in a single or a combination of catalyst particles in direct contact with a suspending liquid medium providing temperature control of the exothermic syngas conversion reaction about the particle of catalyst, recovering heat from said F-T syngas conversion zone in the form of medium pressure steam and utilizing said steam in said coal gasifier or its associated oxygen generation plant;

recovering a product of said Fischer-Tropsch syngas conversion comprising hydrocarbon in a range of $C_1$ to $C_{50}$ hydrocarbons and oxygenates, and converting hydrocarbons and oxygenates recovered from said F-T operation with a special crystalline zeolite catalyst providing a constraint index in the range of 1 to 12, a silica to alumina ratio of at least 12 and a dried crystal density of not less than about 1.6 grams per cubic centimeter to premium products comprising gaseous LPG products, gasoline and distillate material.

2. The process of claim 1 wherein said syngas conversion operation is maintained at a temperature in the range of 400° to 600° F., a pressure in the range of 50 to 700 psig, and a space velocity to achieve at least 50% conversion, and all or a portion of the product of said F-T operation in contact with a ZSM-5 zeolite conversion catalyst maintained at a temperature in the range of 550° to 850° F. and a pressure in the range of 50 to 700 psig and recovering as product of the combination operation a high octane gasoline product and a low pour diesel oil.

3. The process of claim 1 wherein the thermal efficiency of the coal gasification operation is at least 70%.

4. The process of claim 1 wherein a part of the product of syngas conversion is used to suspend the CO reducing catalyst and the crystalline zeolite catalyst is HZSM-5 zeolite.

5. The process of claim 1 wherein the CO reducing component comprises water gas shift activity.

6. The process of claim 1 wherein the CO reducing component is admixed with a water gas shift catalyst component.

7. The process of claim 1 wherein the gaseous hydrocarbons, liquid hydrocarbons and oxygenates of the F-T operation are passed together as a mixture over a bed of ZSM-5 zeolite catalyst for conversion to premium fuels.

8. The process of claim 1 wherein the liquid hydrocarbon product of F-T synthesis is separated to recover gasoline boiling range material from distillate material and each is thereafter separately processed over ZSM-5 zeolite catalyst to produce high octane gasoline and diesel fuel.

9. The process of claim 1 wherein $C_4$ minus gaseous hydrocarbons are processed by one of alkylation or polymerization to produce higher octane gasoline boiling material.

10. The process of claim 1 wherein the gaseous products of F-T synthesis and ZSM-5 catalyst conversion are recovered as SNG and LPG.

11. The process of claim 1 wherein water or steam is added to the F-T conversion zone.

12. The process of claim 1 wherein the light gaseous products of the F-T operation comprising $H_2$, CO and $C_2$ minus hydrocarbons are cryogenically separated, the separated separated $H_2$ and CO gases are recycled to the Fischer-Tropsch operation and a portion of the $C_2$ minus hydrocarbons is used as fuel gas in the processing combination.

* * * * *

UNITED STATES PATENT AND TRADEMARK OFFICE
CERTIFICATE OF CORRECTION

PATENT NO. : 4,252,736

DATED : February 24, 1981

INVENTOR(S) : Werner O. HAAG, Tracy J. HUANG, James W. KUO

It is certified that error appears in the above–identified patent and that said Letters Patent are hereby corrected as shown below:

Column 22, line 9, delete "separated" (first occurrence)

Signed and Sealed this

Fourth Day of August 1981

[SEAL]

Attest:

GERALD J. MOSSINGHOFF

Attesting Officer

Commissioner of Patents and Trademarks